United States Patent [19]

Mach et al.

[11] Patent Number: 5,837,482
[45] Date of Patent: Nov. 17, 1998

[54] CULTURE MEDIUM AND METHODS FOR DETECTING STAPHYLOCOCCI

[75] Inventors: Patrick A. Mach, Shorewood; Marlys E. Lund, Eden Prairie, both of Minn.

[73] Assignee: Minnesota Mining and Manufacturing Company, St. Paul, Minn.

[21] Appl. No.: 785,398

[22] Filed: Jan. 23, 1997

[51] Int. Cl.[6] .............................. C12Q 1/04; C12Q 1/02; C12Q 1/54; C12Q 1/00
[52] U.S. Cl. .............................. 435/34; 435/29; 435/14; 435/4; 435/30; 435/31; 435/32; 435/36; 435/882; 435/883; 435/884; 435/832; 435/833; 435/835; 435/836; 435/837; 435/838; 435/839; 435/283.1; 435/287.1; 536/17.3; 536/17.4
[58] Field of Search ................................ 435/34, 29, 14, 435/4, 30, 31, 32, 36, 882, 883, 884, 832, 833, 834, 835, 836, 837, 838, 839, 283.1, 287.1; 536/17.3, 17.4

[56] References Cited

U.S. PATENT DOCUMENTS

| | | | |
|---|---|---|---|
| 4,444,883 | 4/1984 | Brown et al. | 435/34 |
| 4,565,783 | 1/1986 | Hansen et al. | 435/299 |
| 4,591,554 | 5/1986 | Koumura et al. | 435/34 |
| 5,089,413 | 2/1992 | Nelson et al. | 435/254 |
| 5,210,022 | 5/1993 | Roth et al. | 435/34 |
| 5,358,854 | 10/1994 | Ferguson | 435/34 |
| 5,364,767 | 11/1994 | Flowers et al. | 435/34 |
| 5,393,662 | 2/1995 | Roth et al. | 435/34 |
| 5,443,963 | 8/1995 | Lund | 435/34 |

FOREIGN PATENT DOCUMENTS

| | | |
|---|---|---|
| WO 93/12218 | 6/1993 | WIPO . |
| WO 95/20764 | 8/1995 | WIPO . |
| WO 96/14432 | 5/1996 | WIPO . |
| WO 96/15435 | 5/1996 | WIPO . |

OTHER PUBLICATIONS

Article: Arakawa et al., "Chemiluminescent Assay of Various Enzymes Using Indoxyl Derivatives as Substrate and Its Applications to Enzyme Immunoassay and DNA Probe Assay," *Analytical Biochemistry* 199, (1991) pp. 238–242.
Lopez–Camacho et al; Mutation Research; vol. 301(2), pp. 73–77, 1993; "Random Mutagenesis of a Plasmid–Borne Glycosidase Gene and Phenotypic Selection of Mutants in *E. coli*". (Abstract Only).

*Primary Examiner*—Louise N. Leary

[57] ABSTRACT

A medium for detecting staphylococci is described. The medium contains components selective for growing staphylococci, and a glucopyranoside indicator substance in sufficient quantity to distinguish colonies containing Bacillus and other microorganisms from colonies containing staphylococci. Methods of detecting staphylococci utilizing such medium are also described.

25 Claims, No Drawings

5,837,482

CULTURE MEDIUM AND METHODS FOR DETECTING STAPHYLOCOCCI

FIELD OF THE INVENTION

This invention relates to a medium useful in detecting and enumerating staphylococci, including *Staphylococcus aureus,* in a sample, wherein the medium contains an indicator substance in sufficient quantity to distinguish Bacillus colonies from Staphylococcus colonies when the sample is cultured in the medium, and to methods for detecting staphylococci in a sample using such medium.

BACKGROUND OF THE INVENTION

A variety of methods and processes currently are available to determine, identify and enumerate bacteria in different types of samples. For example, methods are available to identify and enumerate coliform bacteria (coliforms) in samples of water, food or dairy products in order to assess the quality of potential contamination levels of those samples.

One approach to distinguish *E. coli,* a specific type of coliform bacteria commonly classified as a gram-negative rod bacteria, from a mixed population of coliforms is reported in U.S. Pat. No. 5,210,022. In that patent, two substrates that form contrasting insoluble precipitates in the presence of two specific bacterial enzymes, beta-galactosidase and beta-glucuronidase, are incorporated in a test medium. The use of these two substrates allows coliforms to be differentiated from *E. coli* because all coliform bacteria produce beta-galactosidase while only *E. coli* produce beta-glucuronidase. As the colonies of different bacteria grow when incubated in the substrate-containing medium, contrasting colored precipitates form around either growing *E. coli* or coliform colonies. Identification of *E. coli* colonies from the other coliform colonies in the mixed population is readily made by the contrasting colors of the precipitated substrates.

A need for such selective differentiation exists for other kinds of bacteria which are pathogenic or which are associated with harmful effects in humans, such as Salmonella, staphylococci, or Streptococcus.

*Staphylococcus aureus* (*S. aureus*) is an important indicator used in the food processing industry. Detection of this organism is important because some strains are known to produce a heat-stable toxin, called staphylococcal enterotoxin, that is associated with a debilitating disease known as staphylococcal food poisoning. In addition, the presence of this organism in processed food can be an indication of post-processing contamination by asymptomatic carriers of the bacteria on skin surfaces and, especially, in the anterior nares.

Because of the importance for the detection of *S. aureus* and other enterotoxigenic staphylococci, efficient, reliable, and accurate identification of staphylococci is needed. The most common medium currently used for detection of staphylococci is egg-yolk-glycine-tellurite-pyruvate agar (EYGTP agar), also called Baird-Parker agar (BPA). This medium utilizes selective and differential media components to differentiate staphylococci from other bacteria found in the food sample. Potassium tellurite and lithium chloride present in BPA inhibit most other bacteria. *S. aureus* in a BPA sample will react with potassium tellurite to produce black colonies, and will react with lecithin in the egg yolk to produce an opaque "halo" around the colony. A black colony with an opaque halo in BPA is considered a "typical" colony. The BPA components thus provide for a combination differential reaction that differentiates *S. aureus* from other bacteria.

Unfortunately, aberrant reactions with *S. aureus* and other bacteria are possible with BPA. The result of false-positive and false-negative reactions in this medium is that a BPA result is considered only a "presumptive" result. The two aberrant reactions are: (1) non-*S. aureus* bacteria can grow on the BPA and give a false-positive reaction (i.e., produces typical colony); and (2) not all *S. aureus* strains are able to react with differential media components to give a "typical" BPA positive reaction (i.e., tellurite positive (black colony), positive egg yolk or lecithinase reaction (opaque halo)). For these reasons, further "confirmation" steps are required from the BPA plate. These methods include procedures to detect the presence of coagulase or of thermostable nuclease. Either method, when used in conjunction with the BPA medium, is considered to be confirmation of the presence or absence of *S. aureus*.

To proceed from the BPA step to confirmation, however, colony types need to be recognized and selected for further testing. Commonly, "typical" colonies are selected for confirmation and representatives of each of the other colony types are also selected for confirmation. Among the non-*S. aureus* bacteria that can produce typical colonies are strains from the genera Bacillus and Enterococcus. Other strains that grow on BPA and can produce atypical colonies include Listeria species and some members of the Enterobacteriaceae family. Even when these strains don't produce the typical colony type on BPA, they will increase the number of "atypical" colonies required to be selected for confirmation testing.

U.S. Pat. No. 5,443,963 describes a method for identifying and enumerating staphylococci in a sample, wherein a culture medium contains an indolylglucopyranoside substrate as an indicator substance. This method exploits the principle that beta-glucosidase produced by staphylococci does not react with the indolylglucopyranoside substrate, while beta-glucosidase produced by other bacteria in the sample does react with the indolylglucopyranoside to produce a characteristic color. This method thus allows for staphylococci to be distinguished from some non-staphylococci in the sample. The method shown in this patent does not, however, distinguish staphylococci from all non-staphylococci potentially present in a test sample. For example, the method shown in this patent does not distinguish staphylococci from Bacillus species present in a test sample. Bacillus, as well as other microorganisms mentioned above, are sources of false-positive, "typical" colonies in media such as BPA used for growing samples suspected of containing *S. aureus*. False-positive results stemming from "typical" non-Staphylococcus colonies thus remain a substantial problem. A culture system that eliminates such false-positive results would be very useful in the field of microbiological testing. False-negative results also remain a significant problem; Staphylococcus species and strains that produce atypical colonies are a source of false-negative results and require that all atypical colony types be tested further in currently used systems. A culture system that could eliminate non-Staphylococcus atypical colonies and at least presumptively identify atypical Staphylococcus colonies would be highly advantageous.

In the efficient detection and enumeration of *S. aureus* in samples, there is thus a need for methodologies that permit conclusive detection of *S. aureus* and elimination of false-positive and false-negative results produced by other microorganisms in a sample.

SUMMARY OF THE INVENTION

In general, the invention features a culture medium for the detection of staphylococci, wherein the culture medium contains an indicator substance present in sufficient quantity to distinguish colonies containing Bacillus microorganisms from colonies containing staphylococci. The medium provides the ability to (1) eliminate (as non-staphylococci—a negative result) colonies of non-staphylococcal microorganisms that previously would have been identified as "typical" colonies requiring further confirmatory testing, (2) eliminate atypical non-staphylococcal colonies that also would otherwise require further testing, and (3) presumptively identify atypical staphylococcal colonies. The invention also features methods of detecting staphylococci in a sample and distinguishing staphylococcal colonies grown from the sample from colonies of other microorganisms, such as Bacillus microorganisms, grown from the sample.

In one aspect, therefore, the invention features a medium useful in detecting staphylococci in a sample, wherein the medium is selective for growing staphylococci and contains a glucopyranoside indicator substance in sufficient quantity to distinguish Bacillus colonies from staphylococcal colonies when the sample is cultured in the medium.

In one preferred embodiment, the medium is in the form of Baird Parker Agar. In another embodiment, the medium is in the form of a dried broth adhered on a self-supporting, waterproof substrate of a thin film culture device. In still another preferred embodiment, the medium is in the form of a calcium pectinate gel.

The glucopyranoside indicator substance preferably is an indolyl glucopyranoside. A preferred colorimetric glucopyranoside indicator substance is 5-bromo-4-chloro-3-indolyl-beta-D-glucopyranoside.

The glucopyranoside indicator substance is present in an amount sufficient to distinguish colonies containing Bacillus microorganisms from colonies containing staphylococci. Typically, the indicator substance is present in a concentration of at least about 100 $\mu$g/mL when the sample is cultured in the nutrient media.

In another aspect, the invention features a method for detecting staphylococci in a sample. The method includes the step of culturing a sample in a selective culture medium under conditions to produce detectable colonies wherein the culture medium contains an indicator substance as described above in an amount sufficient to distinguish colonies containing Bacillus microorganisms from colonies containing staphylococci.

The method may include the further step of confirming the presence of staphylococci in the sample, and may also further include the step of enumerating the staphylococci in the sample. The confirmatory step may include determining whether or not microorganisms grown from the sample exhibit coagulase activity, or whether or not microorganisms grown from the sample exhibit thermostable nuclease activity. The step of determining whether or not colonies grown from the sample exhibit thermostable nuclease activity may preferably include placing, against such colonies an article comprising toluidine blue O, a binder, and unhydrolyzed DNA.

The sample tested in the method may be a food sample, a clinical sample, a veterinary sample, a cosmetic sample, a pharmaceutical sample, an environmental sample, or any other sample in which testing for staphylococci is desired.

Other advantages and features of the invention will be apparent from the following description and from the claims.

DETAILED DESCRIPTION OF THE INVENTION

The present invention exploits the herein first reported observation that a sufficient amount of a glucopyranoside indicator substance in a medium selective for growing staphylococci can distinguish colonies containing Bacillus and other microorganisms from colonies containing staphylococci when a sample containing staphylococci and potentially Bacillus and other microorganisms is cultured in the medium. This unexpected observation permits microorganisms such as Bacillus species—which can produce "typical" colonies in selective media—to be distinguished from staphylococci. It also allows for certain Staphylococcus, which do not produce the presumptive, "typical" result on currently available systems, to be presumptively identified as staphylococcal colonies. This is especially advantageous in the context of testing food, clinical, or many other types of samples where the efficient and reliable detection of enterotoxigenic organisms such as *S. aureus* is extremely important.

The present invention thus includes a medium useful in detecting staphylococci in a sample, wherein the medium is selective for growing staphylococci and contains a glucopyranoside indicator substance present in sufficient amount to distinguish colonies containing Bacillus microorganisms from colonies containing staphylococci. The indicator substance is a glucopyranoside substrate for the beta-glucosidase of non-Staphylococcus microorganisms, and is not hydrolyzed by staphylococci.

Colorimetric indolyl glucopyranosides are preferred glucopyranoside indicator substances for use in the present invention, with 5-bromo-4-chloro-3-indolyl-beta-D-glucopyranoside being the preferred indolyl glucopyranoside.

Other indolyl glucopyranosides that may be suitable for use in the present invention include, for example:

(1) 5-Bromo-6-chloro-3-indoxyl-beta-D-glucopyranoside;

(2) 6-Chloro-3-indoxyl-beta-D-glucopyranoside; or (3) 3-Indoxyl-beta-D-glucopyranoside.

The preferred 5-bromo-4-chloro-3-indolyl-beta-D glucopyranoside is well-suited for use in the present invention because once its glucose moiety is enzymatically cleaved by beta-glucosidase of non-staphylococcal organisms, the remaining portion of the molecule will dimerize and precipitate in close proximity to the colony to produce a color change. Compounds (1)–(3) above also exhibit this precipitation phenomenon and are thus expected also to be well-suited for use in the medium of the invention. These compounds are preferred over indicator substances that do not precipitate and consequently diffuse away from the colony, complicating the detection of the indicator. In general, any glucopyranoside substance that (1) reacts with the beta-glucosidase of nonstaphylococcal microorganisms but does not react with staphylococcal beta-glucosidase, and (2) provides a detectable signal when its glucose moiety is enzymatically cleaved, will serve as a suitable glucopyranoside indicator substance.

The indicator substance must be present in an amount sufficient to distinguish colonies containing Bacillus microorganisms from colonies containing staphylococci. Examples of microorganisms in addition to Bacillus that are distinguished from staphylococci in accordance with this invention include Enterococcus, Listeria, and some members of the family Enterobacteriaceae (including Proteus, Enterobacter, Serratia, and Klebsiella). As described herein, the invention contemplates that the indicator substance, when present in sufficient quantity to distinguish Bacillus, Listeria, and Enterobacteriaceae, will distinguish any non-Staphylococcus, beta-glucosidase positive microorganism from staphylococci.

Of the selective growth media systems currently known in the art for detecting and enumerating staphylococci, none is able to distinguish "typical" colonies of Bacillus and many other genera of microorganisms from staphylococci. Unexpectedly, the inclusion of certain glucopyranoside indicator substances in sufficient amount permits such microorganisms to be distinguished from staphylococci. In addition, none are able to presumptively identify atypical colonies as staphylococci in BPA-type media; certain Staphylococcus species produce such "atypical" colonies. In the practice of the present invention, such colonies will be presumptively identified as staphylococci.

In general, the indicator substance should be present in a concentration that approaches the solubility limit of the substance in the culture medium when the sample is cultured. This maximizes the possibility that all non-Staphylococcus beta-glucosidase positive organisms will be detected, stained, and distinguished from staphylococcal colonies from the sample. For the indolyl glucopyranosides, including the preferred 5-bromo-4-chloro-3-indolyl-beta-D-glucopyranoside, the concentration should be at least about 100 µg/mL when the sample is being cultured. Those skilled in the art will appreciate that the optimum concentration of the indolyl glucopyranoside indicator substance in the culture medium might vary depending on the particular indicator molecule being used, and that such concentrations may be adjusted and optimized as a routine matter.

In one embodiment of the invention, the medium of the invention may be in the form of an agar gel wherein the selective nutrient medium including the differential indicator substance is contained within agar. One example of a preferred agar gel is Baird Parker Agar, which is described above and is well known in the field of Staphylococcus testing. The practice of the claimed invention in a Baird Parker Agar application is illustrated below in Example 1. In general, in a Baird Parker application utilizing the medium of the invention, non-staphylococcal colonies, including Bacillus and the others mentioned above, will stain the characteristic color of produced by the glucopyranoside indicator substance (e.g. blue or green if 5-bromo-4-chloro-3-indolyl-beta-D-glucopyranoside is used as the indicator) and these colonies can be dismissed as negative. Colonies that are black, whether "typical" or not, are presumed to be staphylococci (including potentially S. aureus), and may be selected for further testing.

In another embodiment, the medium may be in the form of a thin film culture plate device, such as a 3M PETRIFILM™ culture device. Two exemplary embodiments of a thin film culture plate device are (1) a powdered-media-coated thin film device, in which a powder comprising nutrient media components and gelling agents is adhered to a self-supporting, waterproof thin film support and a top film, each film containing a noninhibitory adhesive, and (2) a broth-coated thin film device, in which a nutrient broth is coated on to a self-supporting, waterproof thin film substrate, at pre-selected coating weights for the medium components, and dried; a top film containing gelling agents and optionally staining agents adhered thereto is provided to cover the sample during incubation. A styrofoam layer having an aperture therethrough, may be disposed between the top and bottom films such that the aperture forms a well for the cultured sample. In the use of thin film culture devices such as the 3M PETRIFILM™ devices, a one milliliter sample volume, or inoculum, is standard.

Thin film culture devices, including broth- and powder-coated devices, are fully described in 3M U.S. Pat. No. 4,565,783, the entire disclosure of which is incorporated herein by reference.

A preferred selective media for use in detecting staphylococci in a thin film culture device includes suitable nutrients, salts, and ions needed for staphylococci to produce detectable colonies as well as inhibitors to prevent growth of other undesired microorganisms. Suitable nutrients, salts and ions include, as nonlimiting examples, tryptose peptone, dipeptone, yeast extract, and pyruvic acid. Selected inhibitors are included in the medium to prevent the growth of undesired microorganisms including, but not limited to, gram-negative bacteria such as E. coli, as well as most gram-positive bacteria. Inhibition of these undesired bacteria allows the growth of staphylococci to be selectively enhanced. Suitable inhibitors include a variety of well known antimicrobial or antibiotic compounds. For example, quinoline-based antibacterial compounds such as nalidixic acid, polymyxin-derived compounds such as colistin methanesulfonate, antibiotic compounds such a ceftazidime, and salts such as lithium chloride are known, preferred inhibitors.

The thin film culture device also includes gel-forming agents to provide a solid culture medium. A solid medium provides a defined area for growth of bacterial colonies that may be present in a sample. Suitable gel-forming agents include commercially available agar and gel-forming gums, such as xanthan gum locust bean gum, rhamsan gum, guar gum, and mixtures thereof.

The practice of the present invention in a thin film culture device application is illustrated below in Example 4.

In embodiments of the invention in which the nutrient media is in the form of a thin film culture device, such as, for example, a PETRIFILM™ Staphylococcus Count plate, the indicator substance is included in a sufficient amount such that when a volume of a sample, e.g. one milliliter, is placed on the device, the indicator substance will be present in the culture medium at the desired concentration (see Examples below for exemplary preparation protocols). Following incubation of a sample in such a thin film culture device, staphylococcal colonies will stain red (by the tetrazolium dye included on the top film, see Examples below), while non-staphylococcal colonies will stain the characteristic color of the glucopyranoside indicator substance. If 5-bromo-4-chloro-3-indolyl-beta-D-glucopyranoside is used as the indicator substance, the non-staphylococcal colonies, including Bacillus and others mentioned above, will stain the characteristic blue or green color. At this point, all blue or green colonies can be dismissed as negative for staphylococci, while all red colonies are presumptively staphylococci. If all colonies stain blue or green, the sample is negative for staphylococci and no further testing is required.

Another suitable culture format for practicing the claimed invention is a non-agar, calcium pectinate culture system, such as the REDIGEL™ system, containing, for example, Baird Parker type differential detection reagents. The practice of the claimed invention in a REDIGEL™ format is illustrated below in Example 3.

In the practice of the invention, a culture medium in a culturing device as described herein is inoculated with a test sample. For the purposes of this description, it is assumed that the culture medium contains an indolyl glucopyranoside as an indicator substance. The test sample may be a food, clinical, veterinary, cosmetic pharmaceutical, or environmental sample, or any other sample in which testing for staphylococci is needed or desired. The preparation of such samples for microbiological testing is well known in the art.

The sample is cultured for a time (for example, between about 18–48, hours) and under conditions (for example, between about 30°–37° C.) to allow microorganisms from the sample to form detectable colonies in the culture medium. As the colonies grow in the presence of the indicator substance, all colonies of beta-glucosidase positive, non-staphylococcal microorganisms will develop a characteristic color, such as blue or green, as a consequence of beta-glucosidase reaction with the glucopyranoside substrate. Staphylococcus colonies will not develop the characteristic color, because while they produce a beta-glucosidase, they do not produce an enzyme that hydrolyzes this particular glucopyranoside substrate.

If all colonies in the culture medium develop the characteristic color based on reaction with the glucopyranoside indicator substance, the sample is negative for staphylococci and no further testing is required. If certain colonies in the culture medium appear typical and do not develop the characteristic, these colonies are presumptive Staphylococcus colonies, may include enterotoxigenic or potentially enterotoxigenic microorganisms such as *S. aureus,* and could be selected for further confirmatory testing to determine, for example, if enterotoxigenic or potentially enterotoxigenic staphylococci are present. If certain colonies in the culture medium appear atypical but nonetheless do not stain blue or green, these colonies also are presumptive staphylococci and could be selected for such further testing.

The confirmation of a presumptive Staphylococcus colony may be achieved by several known methods. The colony may be tested to determine whether or not it exhibits coagulase activity or whether or not it exhibits thermostable nuclease activity. A positive result for either coagulase or thermostable nuclease activity is considered to be confirmation of the presence of staphylococci. A number of methods for determining the presence or absence of coagulase or thermostable nuclease activity are well known in the art.

In addition to those methods known in the art, one preferred means of confirming the presence of staphylococci by determining the presence or absence of thermostable nuclease activity in a cultured sample involves placing an article containing toluidine blue (a metachromatic dye that stains differentially in the presence of hydrolyzed or unhydrolyzed DNA), unhydrolyzed DNA, and a binder against colonies in a sample after the sample has been heated to a temperature sufficient to inactivate nonthermostable nucleases. A nonlimiting example of a preferred formulation for such an article and its use is illustrated as follows:

| Ingredients | |
|---|---|
| DNA (Difco Laboratories, Detroit, MI) | 3.6 g/L |
| Toluidine blue O (TBO, Sigma Chemical Company, St. Louis, MO) | 0.32 g/L |
| Calcium chloride, anhydrous (Sigma, St. Louis, MO) | 1.1 mg/L |
| Sodium chloride (Sigma, St. Louis, MO) | 10 g/L |
| Tris hydrochloride (Sigma, St. Louis, MO) | 6.85 g/L |
| Tris base (Sigma, St. Louis, MO) | 0.8 g/L |
| Lambda carrageenan (Sigma, St. Louis, MO) | 0.4 g/L |
| Guar gum (binder) (Rhone-Poulenc Food Ingredients, Cranbury, NJ) | 10 g/L |
| | pH 7.3 or 9.0 |

In preparing the article, all reagents (less the TBO and guar gum) may be mixed together in 1 liter of deionized water. The suspension is mixed with constant stirring and heated to boiling. The TBO is added to the mixture and removed from the heat while maintaining the stirring. The suspension is then mixed with an air mixer (with vigorous vortex) and the guar gum (binder) is added and mixed until uniform. The suspension is cooled overnight at 4° C. and then coated with a knife coater onto 0.18 mm polyester film. Knife gaps of 0.12–0.25 mm are evaluated (coating weights of 0.05–0.10 g/24 square inches). Films are heat dried for 2–10 minutes at 93° C. Articles which may have a thickness of between about 0.12 mm to 0.25 mm, may then be cut to desired shape from the dried film.

Following incubation of a sample in the medium of the invention, the cultured sample is heat-treated to inactivate non-thermostable nucleases, for: example at 60° C. for 30 minutes. The article is then placed against the sample. If Staphylococcus are present, a characteristic red or pink color change will develop around the colony within about 1 to 4 hours under proper conditions. A red or pink color change is considered confirmation of the presence of enterotoxigenic or potentially enterotoxigenic staphylococci, such as *S. aureus.* Such an article and its use are described and claimed in commonly owned 3M U.S. patent application Ser. No. 08/696,385, the entire disclosure of which is incorporated herein by reference.

If the presence of staphylococci in the sample is confirmed, the number of staphylococcal colonies in the cultured sample and the number of staphylococci present in the original sample may be determined using any of a variety of known methods of quantification.

The invention may be illustrated by way of the following Examples.

EXAMPLES

The following microbial strains (Table 1) were used in the experiments described in the Examples below.

TABLE 1

| Species | Strain Designation | Source |
|---|---|---|
| *Bacillus amyloliquefaciens* | 23842 | ATCC[2] |
| *Bacillus cereus* | 11778 | ATCC[2] |
| *Bacillus cereus* | 13061 | ATCC[2] |
| *Bacillus cereus* | 14579 | ATCC[2] |
| *Bacillus circulans* | 61 | ATCC[2] |
| *Bacillus circulans* | 4513 | ATCC[2] |
| *Bacillus coagulans* | 7050 | ATCC[2] |
| *Bacillus licheniformis* | 14580 | ATCC[2] |
| *Bacillus megaterium* | 14581 | ATCC[2] |
| *Bacillus mycoides* | 6462 | ATCC[2] |
| *Bacillus polymyxa* | 842 | ATCC[2] |
| *Bacillus pumilis* | 72 | ATCC[2] |
| *Bacillus sphaericus* | 4525 | ATCC[2] |
| *Bacillus subtilis* | 6051 | ATCC[2] |
| *Bacillus subtilis* | 23059 | ATCC[2] |
| *Bacillus subtilis* | 23856 | ATCC[2] |
| *Bacillus subtilis* | 23857 | ATCC[2] |
| *Bacillus subtilis* | 23858 | ATCC[2] |
| *Bacillus subtilis* | 23859 | ATCC[2] |
| *Bacillus subtilis* | 29056 | ATCC[2] |
| *Bacillus species* | bb | Food isolate[1] |
| *Bacillus species* | L1 | Food isolate[1] |
| *Bacillus species* | L2 | Food isolate[1] |
| *Bacillus species* | L3 | Food isolate[1] |
| *Bacillus species* | L4 | Food isolate[1] |
| *Bacillus species* | L5 | Food isolate[1] |
| *Bacillus species* | L6 | Food isolate[1] |
| *Bacillus species* | L7 | Food isolate[1] |
| *Bacillus species* | L8 | Food isolate[1] |
| *Bacillus species* | L9 | Food isolate[1] |
| *Bacillus species* | L10 | Food isolate[1] |
| *Bacillus species* | L11 | Food isolate[1] |
| *Bacillus species* | L12 | Food isolate[1] |
| *Bacillus species* | L13 | Food isolate[1] |
| *Bacillus species* | L14 | Food isolate[1] |
| *Bacillus species* | L16 | Food isolate[1] |
| *Bacillus species* | L17 | Food isolate[1] |
| *Bacillus species* | L18 | Food isolate[1] |
| *Bacillus species* | L19 | Food isolate[1] |
| *Bacillus species* | L20 | Food isolate[1] |

TABLE 1-continued

| Species | Strain Designation | Source |
|---|---|---|
| Bacillus species | L21 | Food isolate[1] |
| Bacillus species | L22 | Food isolate[1] |
| Bacillus species | L23 | Food isolate[1] |
| Bacillus species | L24 | Food isolate[1] |
| Bacillus species | L25 | Food isolate[1] |
| Bacillus species | L26 | Food isolate[1] |
| Bacillus species | L27 | Food isolate[1] |
| Bacillus species | 1L28 | Food isolate[1] |
| Bacillus species | L29 | Food isolate[1] |
| Bacillus species | L30 | Food isolate[1] |
| Bacillus species | LK1 | Food isolate[1] |
| Bacillus species | LK2 | Food isolate[1] |
| Bacillus species | LK3 | Food isolate[1] |
| Bacillus species | LK4 | Food isolate[1] |
| Bacillus species | LK5 | Food isolate[1] |
| Enterococcus faecium | 882 | ATCC[2] |
| Enterococcus faecium | 19434 | ATCC[2] |
| Enterococcus fecaelis | 29212 | ATCC[2] |
| Enterococcus fecaelis | 14990 | ATCC[2] |
| Enterococcus fecaelis | 19433 | ATCC[2] |
| Enterococcus fecaelis | MMM | Food isolate[1] |
| Enterococcus species | P89 | Clinical isolate[3] |
| Enterococcus species | P90 | Clinical isolate[3] |
| Enterococcus species | P91 | Clinical isolate[3] |
| Enterococcus species | P92 | Clinical isolate[3] |
| Enterococcus species | P93 | Clinical isolate[3] |
| Enterococcus species | P94 | Clinical isolate[3] |
| Enterococcus species | P88 | Clinical isolate[3] |
| Enterococcus species | M1026 | Clinical isolate[3] |
| Enterococcus species | M1028 | Clinical isolate[3] |
| Enterococcus species | M1030 | Clinical isolate[3] |
| Enterococcus species | M1032 | Clinical isolate[3] |
| Enterococcus species | M1038 | Clinical isolate[3] |
| Enterococcus species | M1040 | Clinical isolate[3] |
| Enterococcus species | M1044 | Clinical isolate[3] |
| Enterococcus species | M1148 | Clinical isolate[3] |
| Enterococcus species | M2017 | Clinical isolate[3] |
| Enterococcus species | M2022 | Clinical isolate[3] |
| Enterococcus species | M1144 | Clinical isolate[3] |
| Enterococcus species | M1067 | Clinical isolate[3] |
| Enterococcus species | M1062 | Clinical isolate[3] |
| Staphylococcus aureus | 25923 | ATCC[2] |
| Staphylococcus aureus | W-832 | ATCC[2] |
| Staphylococcus aureus | 13301 | ATCC[2] |
| Staphylococcus aureus | 13565 | ATCC[2] |
| Staphylococcus aureus | 12600 | ATCC[2] |
| Staphylococcus aureus | 27659 | ATCC[2] |
| Staphylococcus aureus | 12598 | ATCC[2] |
| S. epidermidis | 12228 | ATCC[2] |
| S. epidermidis | 14990 | ATCC[2] |
| S. epidermidis | 35547 | ATCC[2] |
| Klebsiella pneumoniae | U28 | Clinical isolate |
| Klebsiella oxytoca | U33 | Clinical isolate |
| Listeria grayi | 11120 | ATCC[2] |
| Listeria innocua | 33091 | ATCC[2] |
| Listeria ivanovii | 19119 | ATCC[2] |
| Listeria ivanovii | 19919 | ATCC[2] |
| Listeria monocytogenes | 13932 | ATCC[2] |
| Listeria monocytogenes | 15313 | ATCC[2] |
| Listeria monocytogenes | 19112 | ATCC[2] |
| Listeria monocytogenes | 19118 | ATCC[2] |
| Listeria monocytogenes | 43256 | ATCC[2] |
| Listeria monocytogenes | 49594 | ATCC[2] |
| Listeria murrayi | 25401 | ATCC[2] |
| Proteus vulgaris | U61 | Clinical isolate[3] |
| Proteus vulgaris | U62 | Clinical isolate[3] |
| Proteus vulgaris | U63 | Clinical isolate[3] |

[1] Food isolate in 3M ™ Microbiology Products Laboratory culture collection, 3M Center, Saint Paul, MN
[2] American Type Culture Collection, Rockville, MD
[3] University of Minnesota Clinical Microbiology culture collection, Minneapolis, MN

Example 1

Baird Parker Agar Application

This Example illustrates the practice of the claimed invention in a Baird Parker Agar application.

Materials:

| | |
|---|---|
| Baird Parker Agar(BPA) | Difco Laboratories, Detroit, MI |
| Bacto Egg yolk-Tellurite Suspension(EYT) | Difco Laboratories, Detroit, MI |
| 5-Bromo-4-Chloro-3-Indolyl-beta-D-Glucopyranoside (BCIG) | Biosynth International, Chicago, IL |
| Dimethyl Formamide(DMF) | Fisher Scientific, Fairlawn, NJ |
| Tryptic Soy Broth tubes | DiMed Laboratories, St. Paul, MN |
| Tryptic Soy Agar plates | DiMed Laboratories, St. Paul, MN |

Method:

One hundred twenty-six g of BPA powder (Difco Laboratories) were weighed and mixed with 2 liters of deionized water according to the manufacturer's recipe. One hundred milligrams of BCIG were weighed into a 16×150 millimeter glass screw cap tube. Ten milliliters of DMF were added to the BCIG powder and vortexed vigorously. Suspension was brought to 60° C. in a water bath and incubated until the powder was dissolved. The mixed and heated BPA powder was sampled into eight, 200 milliliter aliquots in 500 milliliter volume, glass, autoclavable containers. Into the first seven containers were added (into separate containers) 2 milliliters, 1 milliliter, 0.5 milliliters, 0.25 milliliters, 0.125 milliliters, 0.0625 milliliters, and 0.0313 milliliters of the 10 milligram/milliliter BCIG solution. To the final BPA aliquot, no BCIG was added. The containers were autoclaved at 121° C. for 15 minutes at 15 atmospheres. All eight containers were tempered to 46° C. While tempering, Bacto Egg Yolk-Tellurite (EYT) suspension was warmed to 46° C. from 2°–8° C. After the BPA reached 46° C., 10 milliliters of the EYT suspension was added to each container. The containers were swirled gently to mix the EYT into the molten agar. Twenty milliliters of the BCIG media were added to each of nine 15×150-millimeter petri dishes. After the plates were poured and allowed to solidify, the plates were inverted and incubated overnight at room temperature, prior to using.

Bacterial cultures were streaked onto TSA streak plates and incubated at 37° C. overnight. These same plates were used for repeated experiments and were maintained at 2°–8° C. Plates were warmed to room temperature prior to assay. BCIG/BPA plates were divided into eight, equal, pie-shaped sections. Isolated colonies were selected from the TSA plate and streaked onto the BCIG/BPA plates; one colony per BCIG/BPA section per concentration. Plates were incubated at 37° C. for 48 hours. Observations were made on plates after 48 hours and are reported in Table 2.

TABLE 2

| | | BPA (BCIG concentration in ug/mL) | | | | | | |
|---|---|---|---|---|---|---|---|---|
| Strain | Species | 0 | 100 | 50 | 25 | 12.5 | 6.3 | 3.1 | 1.6 |
| 27660 | S. aureus | T[1] | T | T | T | T | T | T | T |
| 13301 | S. aureus | T | T | T | T | T | T | T | T |
| 13565 | S. aureus | T | T | T | T | T | T | T | T |
| 12600 | S. aureus | B[2] | B | B | B | B | B | B | B |
| 27659 | S. aureus | T | T | T | T | T | T | T | T |
| W-832 | S. aureus | T | T | T | T | T | T | T | T |
| 12598 | S. aureus | T | T | T | T | T | T | T | T |

TABLE 2-continued

| | | BPA (BCIG concentration in ug/mL) | | | | | | |
|---|---|---|---|---|---|---|---|---|
| Strain | Species | 0 | 100 | 50 | 25 | 12.5 | 6.3 | 3.1 | 1.6 |
| 25923 | S. aureus | T | T | T | T | T | T | T | T |
| 19433 | E. fecaelis | B | G[3] | G | B | B | B | B | B |
| MMM | E. fecaelis | B | G | G | G | B | B | B | B |
| 882 | E. faecium | B | G | G | G | B | B | B | B |
| 19434 | E. faecium | B | G | G | G | B | B | B | B |
| P88 | E. species | B | G | B | B | B | B | B | B |
| P89 | E. species | B | G | B | B | B | B | B | B |
| P90 | E. species | B | G | B | B | B | B | B | B |
| P91 | E. species | B | G | B | B | B | B | B | B |
| P92 | E. species | B | G | G | B | B | B | B | B |
| P93 | E. species | B | G | G | B | B | B | B | B |
| P94 | E. species | B | G | G | B | B | B | B | B |
| M1026 | E. species | B | G | G | B | B | B | B | B |
| M1028 | E. species | B | G | G | B | B | B | B | B |
| M1030 | E. species | B | G | G | B | B | B | B | B |
| M1032 | E. species | B | G | G | B | B | B | B | B |
| M1038 | E. species | B | G | G | G | B | B | B | B |
| L3 | B. species | B | G | B | B | B | B | B | B |
| L4 | B. species | B | G | G | B | B | B | B | B |
| L8 | B. species | B | G | B | B | B | B | B | B |
| L9 | B. species | B | G | G | B | B | B | B | B |
| L11 | B. species | B | G | B | B | B | B | B | B |
| L12 | B. species | B | G | B | B | B | B | B | B |
| L13 | B. species | B | G | B | B | B | B | B | B |
| L14 | B. species | B | G | B | B | B | B | B | B |
| L18 | B. species | B | G | B | B | B | B | B | B |
| L20 | B. species | B | G | B | B | B | B | B | B |
| L24 | B. species | B | G | B | B | B | B | B | B |
| L27 | B. species | B | G | G | B | B | B | B | B |
| LK1 | B. species | B | G | B | B | B | B | B | B |
| LK3 | B. species | B | G | B | B | B | B | B | B |
| LK4 | B. species | B | G | B | B | B | B | B | B |
| LK5 | B. species | B | G | G | B | B | B | B | B |

[1]Typical colonies
[2]Non-typical colonies with black precipitate
[3]Non-typical colonies with blue-green precipitate with or without black precipitate Example 2

Additional strains were tested with BCIG/BPA media at 0 and 100 micrograms/milliliter. Sixty-three grams of BPA powder (Difco Laboratories) were weighed and mixed with 950 milliliters of deionized water according to the manufacture's recipe. One hundred milligrams of BCIG were weighed into a 16×150 mm glass screw cap tube. Ten milliliters of DMF were added to the BCIG powder and vortexed vigorously. The suspension was brought to 60° C. in a water bath and incubated until the powder was dissolved. The mixed and heated BPA powder was sampled into two 425-milliliter aliquots in 1000 milliliter volume, glass, autoclavable containers. Into one container was added 5.0 milliliters of the 10 milligram/milliliter BCIG solution. To the other BPA aliquot, no BCIG was added. The containers were autoclaved at 121° C. for 15 minutes at 15 atmospheres. Both containers were tempered to 46° C. While tempering, Bacto Egg Yolk-Tellurite (EYT) suspension was warmed to 46° C. from 2°–8° C. The BPA reached 46° C. and twenty-five milliliters of the EYT suspension was added to each container. The containers were swirled gently to mix the EYT into the molten agar. Twenty milliliters of the BCIG media were added to twenty-five 15×100-millimeter petri dishes. After the plates were poured and allowed to solidify, the plates were inverted and incubated overnight at room temperature prior to using.

Bacterial cultures were streaked onto TSA streak plates and incubated at 37° C. overnight. These same plates were used for repeated experiments and were maintained at 2°–8° C. Plates were warmed to room temperature prior to assay. BCIGBPA plates were divided into eight, equal, pie-shaped sections. Isolated colonies were selected from the TSA plate and streaked onto the BCIGIBPA plates; one colony per BCIG/BPA section per concentration. Plates were incubated at 37° C. for 48 hours. Observations were made on plates after 48 hours and are reported in Table 3.

TABLE 3

| Strain | Species | 0 μg/ml BCIG/BPA | 100 μg/ml BCIG/BPA |
|---|---|---|---|
| 23842 | B. amyloliquefaciens | B[1] | G[2] |
| 11778 | B. cereus | B | B* |
| 13061 | B. cereus | B | B* |
| 14579 | B. cereus | B | B* |
| 61 | B. circulans | B | G |
| 4513 | B. circulans | B | G |
| 7050 | B. coagulans | B | |
| 14580 | B. licheniformis | B | G |
| 14581 | B. megaterium | ng[3] | ng |
| 6462 | B. mycoides | B | B* |
| 842 | B. polymyxa | B | G |
| 72 | B. pumilis | B | G |
| 4525 | B. sphaericus | B | B* |
| 6051 | B. subtilis | B | G |
| 23059 | B. subtilis | B | G |
| 23856 | B. subtilis | B | G |
| 23857 | B. subtilis | B | G |
| 23858 | B. subtilis | B | G |
| 23859 | B. subtilis | B | G |
| 29056 | B. subtilis | B | G |
| BB | B. species | B | G |
| L1 | B. species | B | G |
| L2 | B. species | ng | ng |
| L3 | B. species | B | G |
| L4 | B. species | B | G |
| L5 | B. species | ng | ng |
| L6 | B. species | ng | ng |
| L7 | B. species | ng | ng |
| L8 | B. species | B | G |
| L9 | B. species | B | G |
| L10 | B. species | ng | ng |
| L11 | B. species | B | G |
| L12 | B. species | B | G |
| L13 | B. species | B | G |
| L14 | B. species | B | G |
| L15 | B. species | ng | ng |
| L16 | B. species | B | G |
| L17 | B. species | B | G |
| L18 | B. species | B | G |
| L19 | B. species | ng | ng |
| L20 | B. species | B | G |
| L21 | B. species | ng | ng |
| L22 | B. species | ng | ng |
| L23 | B. species | ng | ng |
| L24 | B. species | B | G |
| L25 | B. species | ng | ng |
| L26 | B. species | ng | ng |
| L27 | B. species | B | G |
| L28 | B. species | ng | ng |
| L29 | B. species | ng | ng |
| L30 | B. species | B | G |
| LK1 | B. species | B | G |
| LK2 | B. species | ng | ng |
| LK3 | B. species | B | G |
| LK4 | B. species | B | G |
| LK5 | B. species | B | G |
| 882 | E. faecium | B | G |
| 19434 | E. faecium | B | G |
| 29212 | E. fecaelis | B | G |
| 14990 | E. fecaelis | B | G |
| 19433 | E. fecaelis | B | G |
| MMM | E. fecaelis | B | G |
| P89 | E. species | B | G |
| P90 | E. species | B | G |
| P91 | E. species | B | G |
| P92 | E. species | B | G |

TABLE 3-continued

| Strain | Species | 0 µg/ml BCIG/BPA | 100 µg/ml BCIG/BPA |
|---|---|---|---|
| P93 | E. species | B | G |
| P94 | E. species | B | G |
| P88 | E. species | B | G |
| M1026 | E. species | B | G |
| M1028 | E. species | B | G |
| M1030 | E. species | B | G |
| M1032 | E. species | B | G |
| M1038 | E. species | B | G |
| M1040 | E. species | B | G |
| M1044 | E. species | B | G |
| M1148 | E. species | B | G |
| M2017 | E. species | B | G |
| M2022 | E. species | B | G |
| M1144 | E. species | B | G |
| M1067 | E. species | B | G |
| M1062 | E. species | B | G |
| 25923 | S. aureus | T[4] | T |
| W-832 | S. aureus | T | T |
| 13301 | S. aureus | T | T |
| 13565 | S. aureus | T | T |
| 12600 | S. aureus | B | B |
| 27659 | S. aureus | T | T |
| 12598 | S. aureus | T | T |
| 12228 | S. epidermidis | B | B |
| 14990 | S. epidermidis | B | B |
| 35547 | S. epidermidis | B | B |
| U28 | Klebsiella pneumoniae | B | G |
| U33 | Klebsiella oxytoca | B | G |
| 11120 | Listeria grayi | B | G |
| 33091 | Listeria innocua | B | G |
| 19119 | Listeria ivanovii | B | G |
| 19919 | Listeria ivanovii | B | G |
| 13932 | Listeria monocytogenes | B | G |
| 15313 | Listeria monocytogenes | B | G |
| 19112 | Listeria monocytogenes | B | G |
| 19118 | Listeria monocytogenes | B | G |
| 43256 | Listeria monocytogenes | B | G |
| 49594 | Listeria monocytogenes | B | G |
| 25401 | Listeria murrayi | B | G |
| U61 | Proteus vulgaris | B | G |
| U62 | Proteus vulgaris | B | G |
| U63 | Proteus vulgaris | B | G |

*BCIG negative strain
[1]Non-typical colonies with black precipitate
[2]Non-typical colonies with blue-green precipitate with or without black precipitate
[3]no growth
[4]Typical colonies Example 3

REDIGEL™ Baird Parker:

This Example illustrates the practice of the claimed invention in a ectinate (REDIGEL™) application.

Materials:

| | |
|---|---|
| Baird-Parker REDIGEL™ (10 plate size) | RCR, Inc., Goshun, IN |
| 5-Bromo-4-Chloro-3-Indolyl-beta-D-Glucopyranoside (BCIG) | Biosynth International, Chicago, IL |
| Dimethyl Formamide(DMF) | Fisher Scientific, Fairlawn, NJ |
| Tryptic Soy Broth tubes | DiMed Laboratories, St. Paul, MN |
| Tryptic Soy Agar plates | DiMed Laboratories, St. Paul, MN |

Method:

REDIGEL™, a commercial product that utilizes calcium pectinate as a gelling matrix for microbial growth and detection, utilizes a system for detection of staphylococci similar to Baird-Parker Agar. The system used for this application was a 10 plate kit that includes 110 milliliters of solution containing the selective and differential reagents in the solution with the pectin and treated petri dishes that contain the calcium required to form the gel matrix for microbial growth. To five bottles of the solution were added the following volumes of 10 milligrams BCIG/milliliter in DMF: 1.1 milliliter, 0.55 milliliters, 0.275 milliliters, 0.1375 milliliters, 0.0688 milliliters, and 0 milliliters. These gave rise to solutions with 100, 50, 25, 12.5, 6.3 and 0 micrograms BCIG per milliliter. Eleven milliliters of each solution were added to nine individual plates. Plates were left upright for 6 hours at room temperature. TSA cultures were then streaked onto the plates as described in the previous section for BPA evaluation. Plates were then incubated at 37° C. and read at 48 hours. Results are recorded in Table 4.

TABLE 4

| | | REDIGEL™ Baird Parker (BCIG concentration in µg/mL) | | | | | |
|---|---|---|---|---|---|---|---|
| Strain | Species | 0 | 100 | 50 | 25 | 12.5 | 6.3 |
| 27660 | S. aureus | T[1] | T | T | T | T | T |
| 13301 | S. aureus | T | T | T | T | T | T |
| 13565 | S. aureus | T | T | T | T | T | T |
| 12600 | S. aureus | B[2] | B | B | B | B | B |
| 27659 | S. aureus | T | T | T | T | T | T |
| W-832 | S. aureus | T | T | T | T | T | T |
| 12598 | S. aureus | T | T | T | T | T | T |
| 25923 | S. aureus | T | T | T | T | T | T |
| 19433 | E. fecaelis | B[1] | G[3] | G | G | G | B |
| MMM | E. fecaelis | B | G | G | G | G | B |
| 882 | E. faecium | B | G | G | G | G | B |
| 19434 | E. faecium | B | G | G | G | G | B |
| P88 | E. species | B | G | G | G | G | B |
| P89 | E. species | B | G | G | G | G | B |
| P90 | E. species | B | G | G | G | G | B |
| P91 | E. species | B | G | G | G | G | B |
| P92 | B. species | B | G | G | G | G | B |
| P93 | E. species | B | G | G | G | G | B |
| P94 | E. species | B | G | G | G | G | B |
| M1026 | E. species | B | G | G | G | G | B |
| M1028 | E. species | B | G | G | G | G | B |
| M1030 | E. species | B | G | G | G | G | B |
| M1032 | E. species | B | G | G | G | G | B |
| M1038 | E. species | B | G | G | G | G | B |
| L3 | B. species | B | G | B | B | B | B |
| L4 | B. species | B | G | G | B | B | B |
| L8 | B. species | B | G | B | B | B | B |
| L9 | B. species | B | G | G | G | B | B |
| L11 | B. species | B | G | G | G | B | B |
| L12 | B. species | B | G | B | B | B | B |
| L13 | B. species | B | G | G | B | B | B |
| L14 | B. species | B | G | G | B | B | B |
| L18 | B. species | B | G | G | B | B | B |
| L20 | B. species | B | G | G | B | B | B |
| L24 | B. species | B | G | B | B | B | B |
| L27 | B. species | B | G | G | G | B | B |
| LK1 | B. species | B | G | G | B | B | B |
| LK3 | B. species | B | G | B | B | B | B |
| LK4 | B. species | B | G | B | B | B | B |
| LK5 | B. species | B | G | G | B | B | B |

[1]Typical colonies
[2]Non-typical colonies with black precipitate
[3]Non-typical colonies with blue-green precipitate with or without black precipitate Example 4

PETRIFILM™ Staphylococcus Count Plate Application With BCIG Titration

This example illustrates the practice of the claimed invention in a thin film culture device.

Materials:

| | |
|---|---|
| PETRIFILM ™ Aerobic Count Top Film | 3M Company, St. Paul, MN |
| Xanthan Gum | Kelco, San Diego, CA |
| Locust Bean Gum | Genu Worldwide, Lille Skensved, Denmark |
| Guar Gum | Meyhall Chemical RG, Zandaam The Netherlands |
| 7.5 mil Melinex | ICI Films, Wilmington, DE |
| Broth Powders: | |
| Tryptose peptone | Acumedia, Baltimore, MD |
| Dipeptone | Acumedia, Baltimore, MD |
| Yeast Extract | BBL, Baltimore, MD |
| Lithium Chloride | Sigma Chemical, St. Louis, MO |
| Nalidixic Acid | Sigma Chemical, St. Louis, MO |
| Ceftazidime | Sigma Chemical, St. Louis, MO |
| Pyruvic Acid | Sigma Chemical, St. Louis, MO |
| Egg Yolk Suspension | Difco Laboratories, Detroit, MI |
| 5-Bromo-4-Chloro-3-Indolyl-beta-D-Glucopyranoside (BCIG) | Biosynth International Naperville, IL |
| 20 mil styrofoam | Astro-Valcour, Inc., Glen Falls, NY |

Titration to determine the effective range of BCIG for differentiation of *S. aureus* from BCIG positive non-*S. aureus* was completed as follows:

Top Film:

Xanthan gum, locust bean gum and guar gum were mixed in a ratio of 2:2:1. This mixture was powder coated onto the PETRIFILM™ Aerobic Count top film, which contains triphenyl tetrazolium chloride, at a level of approximately 0.4 grams per 24 square inches of film.

Broth mixture:

Broth powders were mixed in the following manner:

| | |
|---|---|
| Tryptose peptone | 100 grams |
| Dipeptone | 100 grams |
| Yeast Extract | 40 grams |
| Lithium Chloride | 40 grams |
| Nalidixic acid | 80 milligrams |
| Ceftazidime | 8 milligrams |
| Pyruvic acid | 40 grams |
| Egg Yolk suspension | 80 milliliters |
| Deionized water | 4 liters |

The powders were mixed vigorously into the water. The solution was sampled into eight 500-milliliter aliquots. The following quantities of BCIG were added to separate aliquots and mixed vigorously: 100 milligrams, 75 milligrams, 50 milligrams, 37.5 milligrams, 25 milligrams, and 12.5 milligrams. Five grams of an equal mixture of xanthan gum:guar gum were added to each solution and mixed vigorously. After all powders were added and mixed well, the solutions were heated to 80° C. with vigorous mixing. Solutions were then cooled overnight at 2°–8° C. Broth was coated onto the Melinex through a knife gap of approximately 13 mils and then dried at 93° C. for approximately 10 minutes. Coating weight of 300–350 milligrams per 24 square inches was achieved with this coating. Twenty mil styrofoam was transfer coated with acrylic acid adhesive. Two inch diameter circles were removed from the styrofoam material that will function as a well for holding inoculum. Broth coated web was laminated onto the 20 mil styrofoam. One-half inch double-sided adhesive tape was used as a hinge to adhere the powder-coated top film to the styrofoam/broth-coated Melinex laminant. The films were cut into 3×4 inch rectangles with the circle in the approximate center of the rectangle. Films were gamma irradiated at 5–10 kilograys prior to being evaluated. Bacterial cultures were prepared for evaluation by culturing in tryptic soy broth overnight at 37° C. Appropriate dilutions of the cultures were done to achieve approximately 100 colony forming units (cfu) per milliliter in Butterfields Standard Methods Buffer (Fisher Scientific, Chicago, Il.). The dilutions of each bacterium were compared with results obtained from an equivalent plating on PETRIFILM™ Aerobic Count plate (PAC), with results shown in Table 5. Bacterial dilutions (1.0 milliliter) were plated and counted after 24 hours at 37° C.

TABLE 5

| | | PETRIFILM ™ Staphylococcus Count Plate (BCIG concentration in μg/mL) | | | | | | | |
|---|---|---|---|---|---|---|---|---|---|
| Strain | Species | 0 | 100 | 75 | 50 | 37.5 | 25 | 12.5 | PAC |
| 27660 | *S. aureus* | 92- | 83- | 80- | 83- | 62- | 86- | 76- | 85 |
| 13301 | *S. aureus* | 175- | 154- | 184- | 170- | 193- | 194- | 173- | 184 |
| 13565 | *S. aureus* | 39- | 50- | 44- | 44- | 45- | 51- | 43- | 42 |
| 12600 | *S. aureus* | 120- | 121- | 134- | 132- | 120- | 106- | 112- | 130 |
| 27659 | *S. aureus* | 115- | 122- | 144- | 132- | 127- | 130- | 125- | 166 |
| W-832 | *S. aureus* | 189- | 161- | 159- | 158- | 157- | 170- | 164- | 168 |
| 12598 | *S. aureus* | 115- | 95- | 114- | 106- | 112- | 104- | 92- | 114 |
| 25923 | *S. aureus* | 39- | 49- | 55- | 57- | 59- | 61- | 48- | 54 |
| 19433 | *E. fecaelis* | ng[1] | ng | 3* | 24* | 21* | ng | ng | 137 |
| MMM | *E. fecaelis* | 125- | 98* | 156* | 136* | 145* | 142* | 134* | 205 |
| 882 | *E. faecium* | 41- | 65* | 82* | 69* | 53* | 75* | 69- | 78 |
| 19434 | *E. faecium* | 80- | 41* | 63* | 82* | 91* | 107* | 78- | 131 |
| P88 | *E. species* | 36- | 10* | 25* | 28* | 28* | 34- | 14- | 103 |
| P89 | *E. species* | 16- | 32* | 26* | 13* | 41* | 28- | 21- | 81 |
| P90 | *E. species* | 9- | 3* | 9* | 10* | 20* | 21* | 8* | 115 |
| P91 | *E. species* | 20- | 7* | 28* | 17* | 64* | 35* | ng | 121 |
| P92 | *E. species* | ng | ng | ng | ng | 5* | 22* | ng | 102 |
| P93 | *E. species* | 20- | 2* | 20* | 17* | 12* | 25* | 2- | 80 |
| P94 | *E. species* | 13- | 4* | 29* | 5* | 29* | 34* | 10- | 102 |
| M1026 | *E. species* | 2- | 1* | 2* | 1* | ng | 4* | ng | 62 |
| M1028 | *E. species* | ng | 8* | 16* | 7* | 8* | 25* | 1- | 74 |
| M1030 | *E. species* | 1- | 5* | ng | ng | 20* | 28* | 1- | 146 |

TABLE 5-continued

| | | PETRIFILM ™ Staphylococcus Count Plate (BCIG concentration in µg/mL) | | | | | | | |
|---|---|---|---|---|---|---|---|---|---|
| Strain | Species | 0 | 100 | 75 | 50 | 37.5 | 25 | 12.5 | PAC |
| M1032 | E. species | ng | 6* | 1* | 4* | 7* | 6* | ng | 70 |
| M1038 | E. species | 11- | ng | ng | ng | 14* | 7* | ng | 67 |
| L3 | B. species | ng | ng | ng | ng | ng | ng | ng | 210 |
| L4 | B. species | ng | ng | ng | ng | ng | ng | ng | >300 |
| L8 | B. species | ng | ng | ng | ng | ng | ng | ng | >300 |
| L9 | B. species | 139- | 121* | 144* | 153* | 135- | 157- | 135- | 180 |
| L11 | B. species | ng | ng | ng | ng | ng | ng | ng | >300 |
| L12 | B. species | ng | ng | ng | ng | ng | ng | ng | 190 |
| L13 | B. species | ng | ng | ng | ng | ng | ng | ng | 200 |
| L14 | B. species | ng | ng | ng | ng | ng | ng | ng | >300 |
| L18 | B. species | ng | ng | ng | ng | ng | ng | ng | >300 |
| L20 | B. species | ng | ng | ng | ng | ng | ng | ng | >300 |
| L24 | B. species | ng | ng | ng | ng | ng | ng | ng | 250 |
| L27 | B. species | ng | ng | ng | ng | ng | ng | ng | >300 |
| LK1 | B. species | ng | ng | ng | ng | ng | ng | ng | 330 |
| LK3 | B. species | ng | ng | ng | ng | ng | ng | ng | 157 |
| LK4 | B. species | ng | ng | ng | ng | ng | ng | ng | 170 |
| LK5 | B. species | 170- | 150* | 180* | 220* | 190* | 210- | 180- | 270 |

[1]No growth
*Blue to red-blue colonies
-Red colonies only

To evaluate further strains, PETRIFILM™ Staphylococcus Count (PSC) plate formulations were prepared with 0 and 100 micrograms/milliliter BCIG, as follows:
Materials:

| PETRIFILM ™ Aerobic Count Top Film | 3M Company, St. Paul, MN |
|---|---|
| Xanthan Gum | Kelco, San Diego, CA |
| Locust Bean Gum | Genu Worldwide, Lille Skensved Denmark |
| Guar Gum | Meyhall Chemical AG, Zandaam The Netherlands. |
| 7.5 mil Melinex | ICI Films, Wilmington, DE |

Broth Powders:

| Tryptose peptone | Acumedia, Baltimore, MD |
|---|---|
| DiPeptone | Acumedia, Baltimore, MD |
| Yeast Extract | BBL, Baltimore, MD |
| Lithium Chloride | Sigma Chemical, St. Louis, MO |
| Nalidixic Acid | Sigma Chemical, St. Louis, MO |
| Ceftazidime | Sigma Chemical, St. Louis, MO |
| Pyruvic Acid | Sigma Chemical, St. Louis, MO |
| Egg Yolk Suspension | Difco Laboratories, Detroit, MI |
| 5-Bromo-4-Chloro-3-Indolyl-beta-D-Glucopyranoside (BCIG) | Biosynth International, Naperville, IL |
| 20 mil styrofoam | Astro-Valcour, Inc., Glen Falls, NY |

Top Film:
Xanthan gum, locust bean gum and guar gum were mixed in a ratio of 2:2:1. This mixture was powder coated onto the PETRIFILM™ Aerobic Count Top Film, which contains triphenyltetrazolium chloride, at a level of approximately 0.4 grams per 34 square inches of film.
Broth mixture:
Broth powders were mixed in the following manner:

| Tryptose peptone | 50 grams |
|---|---|
| Dipeptone | 50 grams |
| Yeast Extract | 20 grams |
| Lithium Chloride | 20 grams |
| Nalidixic acid | 40 milligrams |
| Ceftazidime | 4 milligrams |
| Pyruvic acid | 20 grams |
| Egg Yolk suspension | 40 milliliters |
| Deionized water | 2 liters |

Powders were mixed vigorously into the water. Solution was sampled into two 1000-milliliter aliquots. Two hundred milligrams of BCIG was added to one of the aliquots and mixed vigorously. Twenty grams of an equal mixture of xanthan gum:guar gum were added to both solutions and mixed vigorously. After all powders were added and mixed well, both solutions were heated to 80° C. with vigorous mixing. Solutions were then cooled overnight at 2°–8° C. Broth was coated onto the Melinex through a knife gap of approximately 10 mils and then dried at 93° C. for approximately 10 minutes. Coating weight of 300–350 milligrams per 24 square inches was achieved with this coating. Twenty-mil styrofoam was transfer coated with acrylic acid adhesive. Two inch diameter circles were removed from the styrofoam material that functioned as a well for holding inoculum. Broth coated web was laminated onto the 20-mil styrofoam. One-half inch double-sided adhesive tape was used as a hinge to adhere the powder-coated top film to the styrofoam/broth-coated Melinex laminant. The films were cut into 3×4 inch rectangles with the circle in the approximate center of the rectangle. Films were gamma irradiated at 5–10 kilograys prior to being evaluated. Bacterial cultures were prepared for evaluation by culturing in tryptic soy broth overnight at 37° C. Appropriate dilutions of the cultures were done to achieve approximately 100 colony forming units (cfu) per milliliter in Butterfields Standard Methods Buffer (Fisher Scientific, Chicago, Il.). The dilutions of each bacterium was computed with results obtained from an equivalent plating on 3M PETRIFILM™ Aerobic Count plate. Bacterial dilutions (1.0 milliliter) were plated in duplicate and counted after 24 hours at 37° C. The results are shown in Table 6.

TABLE 6

| Strain | Species | PAC plate (Mean cfu/milliliter) | PSC plate (Mean cfu/milliliter) |
|---|---|---|---|
| 23842 | B. amyloliquefaciens | 265 | ng[1] |
| 11778 | B. cereus | 86.5 | ng |
| 13061 | B. cereus | 320 | ng |
| 14579 | B. cereus | 215 | ng |
| 61 | B. circulans | 810 | 295* |
| 4513 | B. circulans | 570 | 355* |
| 7050 | B. coagulans | 230 | ng |
| 14580 | B. licheniformis | 208 | 144* |
| 14581 | B. megaterium | ng | ng |
| 6462 | B. mycoides | ng | ng |
| 842 | B. polymyxa | 125 | ng |
| 72 | B. pumilis | 940 | 520* |
| 4525 | B. sphaericus | 165 | 174– |
| 6051 | B. subtilis | 225 | ng |
| 23059 | B. subtilis | 149 | ng |
| 23856 | B. subtilis | 95 | ng |
| 23857 | B. subtilis | >1000 | ng |
| 23858 | B. subtilis | 265 | ng |
| 23859 | B. subtilis | 415 | ng |
| 29056 | B. subtilis | 546 | ng |
| L3 | B. species | 148 | ng |
| L4 | B. species | >1000 | ng |
| L8 | B. species | 230 | ng |
| L9 | B. species | 154 | 137* |
| L11 | B. species | 800 | ng |
| L12 | B. species | 550 | ng |
| L13 | B. species | >1000 | ng |
| L14 | B. species | >1000 | ng |
| L18 | B. species | >1000 | ng |
| L24 | B. species | 630 | ng |
| L27 | B. species | 210 | ng |
| 882 | E. faecium | 26 | 4* |
| 19433 | E. fecaelis | 59 | ng |
| MMM | E. fecaelis | 77 | 16* |
| P89 | E. species | 66 | ng |
| P90 | E. species | 84 | ng |
| P91 | E. species | 49 | ng |
| P92 | E. species | 60 | ng |
| P93 | E. species | 70 | ng |
| P94 | E. species | 59 | ng |
| P88 | E. species | 40 | ng |
| M1026 | E. species | 43 | ng |
| M1028 | E. species | 44 | ng |
| 13301 | S. aureus | 112 | 108– |
| 13565 | S. aureus | 60 | 63– |
| 12600 | S. aureus | 79 | 73– |
| 27659 | S. aureus | 64 | 78– |
| 12598 | S. aureus | 62 | 52– |
| 35547 | S. epidermidis | 24 | 22– |

[1]No growth
*Blue to red-blue colonies
–Red colonies only

Other embodiments of the invention are within the scope of the claims.

What is claimed is:

1. A medium for detecting staphylococci in a sample, said medium comprising components selective for growing staphylococci and egg-yolk as a differential detection agent, said medium further comprising a glucopyranoside indicator substance in an amount sufficient to distinguish colonies containing staphylococci from colonies containing Bacillus microorganisms when said sample is cultured in said medium.

2. The medium of claim 1, wherein said medium is in the form of an agar gel.

3. The medium of claim 2, wherein said agar gel comprises a Baird Parker Agar gel.

4. The medium of claim 1, wherein said medium is in the form of dried broth adhered on a self-supporting, waterproof substrate of a thin film culture device.

5. The medium of claim 1, wherein said medium is in the form of a calcium pectinate gel.

6. The medium of claim 1, wherein said glucopyranoside indicator substance comprises an indolyl glucopyranoside.

7. The medium of claim 2, wherein said indicator substance comprises 5-bromo-4-chloro-3-indolyl-beta-D-glucopyranoside.

8. The medium of claim 1, wherein said glucopyranoside indicator substance is present in a concentration of at least about 100 micrograms per milliliter when said sample is cultured in said medium.

9. A method for detecting staphylococci in a sample, comprising:

culturing said sample in a medium containing components selective for growing staphylococci and egg-yolk as a differential detection agent under conditions to produce detectable colonies, said medium further comprising a glucopyranoside indicator substance in an amount sufficient to distinguish colonies containing staphylococci from colonies containing Bacillus colonies when said sample is cultured in said medium.

10. The method of claim 9, wherein said method further comprises confirming the presence or absence of staphylococci in said sample.

11. The method of claim 9, wherein said method further comprises enumerating the staphylococci in said sample.

12. The method of claim 9, wherein said indicator substance comprises an indolyl glucopyranoside.

13. The method of claim 12, wherein said glucopyranoside indicator substance comprises 5-bromo-4-chloro-3-indolyl-beta-D-glucopyranoside.

14. The method of claim 9, wherein said glucopyranoside indicator substance is present in a concentration of at least about 100 micrograms per milliliter when said sample is cultured in said medium.

15. The method of claim 9, wherein confirming the presence or absence of staphylococci in said sample comprises determining whether or not colonies grown from said sample exhibit coagulase activity.

16. The method of claim 9, wherein confirming the presence or absence of staphylococci in said sample comprises determining whether or not colonies grown from said sample exhibit thermostable nuclease activity.

17. The method of claim 16, wherein determining whether or not colonies grown from said sample exhibit thermostable nuclease activity comprises placing against colonies grown from said sample an article comprising toluidine blue O, a binder, and unhydrolyzed DNA.

18. The method of claim 9, wherein said sample is selected from the group consisting of a food sample, a clinical sample, a veterinary sample, a cosmetic sample, a pharmaceutical sample, a water sample, and an environmental sample.

19. The method of claim 9, wherein said medium is in the form of an agar gel.

20. The method of claim 19, wherein said agar gel comprises a Baird Parker Agar gel.

21. The method of claim 9, wherein said medium is in the form of a calcium pectinate gel.

22. A method for detecting staphylococci in a sample, comprising:

culturing said sample in a medium containing components selective for growing staphylococci under conditions to produce detectable colonies, said medium comprising a glucopyranoside indicator substance in an amount sufficient to distinguish colonies containing staphylococci from colonies containing Bacillus colonies when said sample is cultured in said medium; and confirming the presence or absence of staphylococci in said sample by determining whether or not colonies grown from said sample exhibit coagulase activity.

23. A method for detecting staphylococci in a sample, comprising:

culturing said sample in a medium containing components selective for growing staphylococci under conditions to produce detectable colonies, said medium comprising a glucopyranoside indicator substance in an amount sufficient to distinguish colonies containing staphylococci from colonies containing Bacillus colonies when said sample is cultured in said medium; and confirming the presence or absence of staphylococci in said sample by determining whether or not colonies grown from said sample exhibit thermostable nuclease activity.

24. The method of claim 20, wherein determining whether or not colonies grown from said sample exhibit thermostable nuclease activity comprises placing against colonies grown from said sample an article comprising toluidine blue O, a binder, and unhydrolyzed DNA.

25. The method of claim 22 or 23, wherein said medium is in the form of dried broth adhered on a self-supporting, waterproof substrate of a thin film culture device.

* * * * *

UNITED STATES PATENT AND TRADEMARK OFFICE
CERTIFICATE OF CORRECTION

PATENT NO.   : 5,837,482                                      Page 1 of 1
DATED        : November 17, 1998
INVENTOR(S)  : Patrick A. Mach and Marlys E. Lund It is certified that error appears in the above-identified patent and that said Letters Patent is hereby corrected as shown below:

Column 22:
Line 5, Claim 24, replace "20" with --23--.

Signed and Sealed this

Twelfth Day of June, 2001

*Attest:*

*Attesting Officer*

NICHOLAS P. GODICI
*Acting Director of the United States Patent and Trademark Office*